US00PP37224P2

(12) United States Plant Patent
Holtmaat

(10) Patent No.: US PP37,224 P2
(45) Date of Patent: Jan. 20, 2026

(54) ***RUDBECKIA* PLANT NAMED 'RUDBBCH767'**

(50) Latin Name: *Rudbeckia hirta*
Varietal Denomination: RUDBBCH767

(71) Applicant: Henricus Maria Joseph Holtmaat, Zuidwolde (NL)

(72) Inventor: Henricus Maria Joseph Holtmaat, Zuidwolde (NL)

(73) Assignee: NOVA PERENNE BV, Zuidwolde (NL)

( * ) Notice: Subject to any disclaimer, the term of this patent is extended or adjusted under 35 U.S.C. 154(b) by 0 days.

(21) Appl. No.: 19/232,149

(22) Filed: Jun. 9, 2025

(30) Foreign Application Priority Data

Sep. 30, 2024 (QZ) ..... PBR 20242268

(51) Int. Cl.
*A01H 5/02* (2018.01)
*A01H 6/14* (2018.01)

(52) U.S. Cl.
USPC ..... Plt./474

(58) Field of Classification Search
USPC ..... Plt./474
See application file for complete search history.

(56) References Cited

U.S. PATENT DOCUMENTS

PP30,657 P2 * 7/2019 Holtmaat ..... A01H 6/14
Plt./474

* cited by examiner

*Primary Examiner* — Susan Mccormick Ewoldt
(74) *Attorney, Agent, or Firm* — Penny J. Aguirre

(57) ABSTRACT

A new cultivar of *Rudbeckia* plant named 'RUDBBCH767' that is characterized by its strong and sturdy stems, its compact plant habit, its floriferous blooming habit, its inflorescences with 4 whorls of ray florets, its large inflorescences, and its fast propagation and production time.

2 Drawing Sheets

Botanical classification: *Rudbeckia hirta.*
Variety denomination: 'RUDBBCH767'.

CROSS-REFERENCE TO RELATED APPLICATIONS

This application claims priority to European Community Plant Variety Office (CPVO) Plant Breeder's Rights Application No. 2024/2268 filed on Sep. 30, 2024, under 35 U.S.C. 119(f), the entire contents of which is incorporated by reference herein. This application is co-pending with a U.S. Plant Patent Applications filed for plants derived from the same breeding program that are entitled *Rudbeckia* Plant Named 'RUDBKST704' (U.S. Plant patent application Ser. No. 19/232,186)*, *Rudbeckia* Plant Named 'RUDLPIR734' (U.S. Plant patent application Ser. No. 19/232,300)* and *Rudbeckia* Plant Named 'RUDBSS851' (U.S. Plant patent application Ser. No. 19/232,228)*.
*(Applicant gives the examiner the authority to replace the U.S. Plant Patent pending with an Application No. or Patent No. if applicable and delete this statement.)

BACKGROUND OF THE INVENTION

The present invention relates to a new and distinct cultivar of *Rudbeckia hirta* and will hereafter by referred to by its cultivar name, 'RUDBBCH767'. The new cultivar is an herbaceous perennial grown for use as a landscape plant.

'RUDBBCH767' was selected in June of 2021 as a single unique plant by the Inventor from amongst seedlings in a trial field in Zuidwolde, Netherlands. The trial field had been planted with seed derived from open pollination of numerous unpatented and unnamed proprietary plants from the Inventor's breeding program. The collected seeds were pooled before sowing and therefore the parentage is unknown.

Asexual propagation of the new cultivar was first accomplished under the direction of the Inventor by tissue culture using meristematic tissue in Heerhugowaard, The Netherlands in February of 2024. Asexual propagation by tissue culture has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'RUDBBCH767' as a unique cultivar of *Rudbeckia.*

1. 'RUDBBCH767' exhibits strong and sturdy stems.
2. 'RUDBBCH767' exhibits a compact plant habit.
3. 'RUDBBCH767' exhibits a floriferous blooming habit.
4. 'RUDBBCH767' exhibits inflorescences with 4 whorls of ray florets.
5. 'RUDBBCH767' exhibits large inflorescences.
6. 'RUDBBCH767' exhibits a fast propagation and production time.

'RUDBBCH767' can be compared to the *Rudbeckia* cultivars 'RUDHT37' (U.S. Plant Pat. No. 30,657) and 'RUDLE169' (U.S. Plant Pat. No. 32,918). 'RUDHT37' is similar to 'RUDBBCH767' in having a compact plant habit and yellow ray florets. 'RUDHT37' differs from 'RUDBBCH767' in having inflorescences flowers with one row of ray florets, and a slower propagation and production time. 'RUDLE169' is similar to 'RUDBBCH767' in having strong and sturdy stems and medium green foliage. 'RUDLE169' differs from 'RUDBBCH767' in having a shorter plant height and inflorescences with one row of ray florets.

'RUDBBCH767' can also be compared to the co-pending cultivars of *Rudbeckia*; 'RUDBKST704', 'RUDLPIR734', and 'RUDBSS851'. 'RUDBKST704' differs from 'RUDBBCH767' in having less ray florets that are yellow-orange with a lighter yellow-orange top. 'RUDBSS851' differs from 'RUDBBCH767' in having bi-color ray florets. 'RUDLPIR734' differs from 'RUDBBCH767' in having more ray florets, an inflorescence disc that is fully covered by ray florets, and ray floret colors that are deeper yellow with yellow-orange flushed apexes.

BRIEF DESCRIPTION OF THE DRAWINGS

The accompanying color photographs illustrate the overall appearance and distinct characteristics of the new *Rudbeckia*. The photographs were taken of a 3-month-old plant of 'RUDBBCH767' as grown outdoors in a 23-cm container in Zuidwolde, The Netherlands.

The photograph in FIG. 1 is a side view of 'RUDBBCH767' in bloom.

Figure 1:
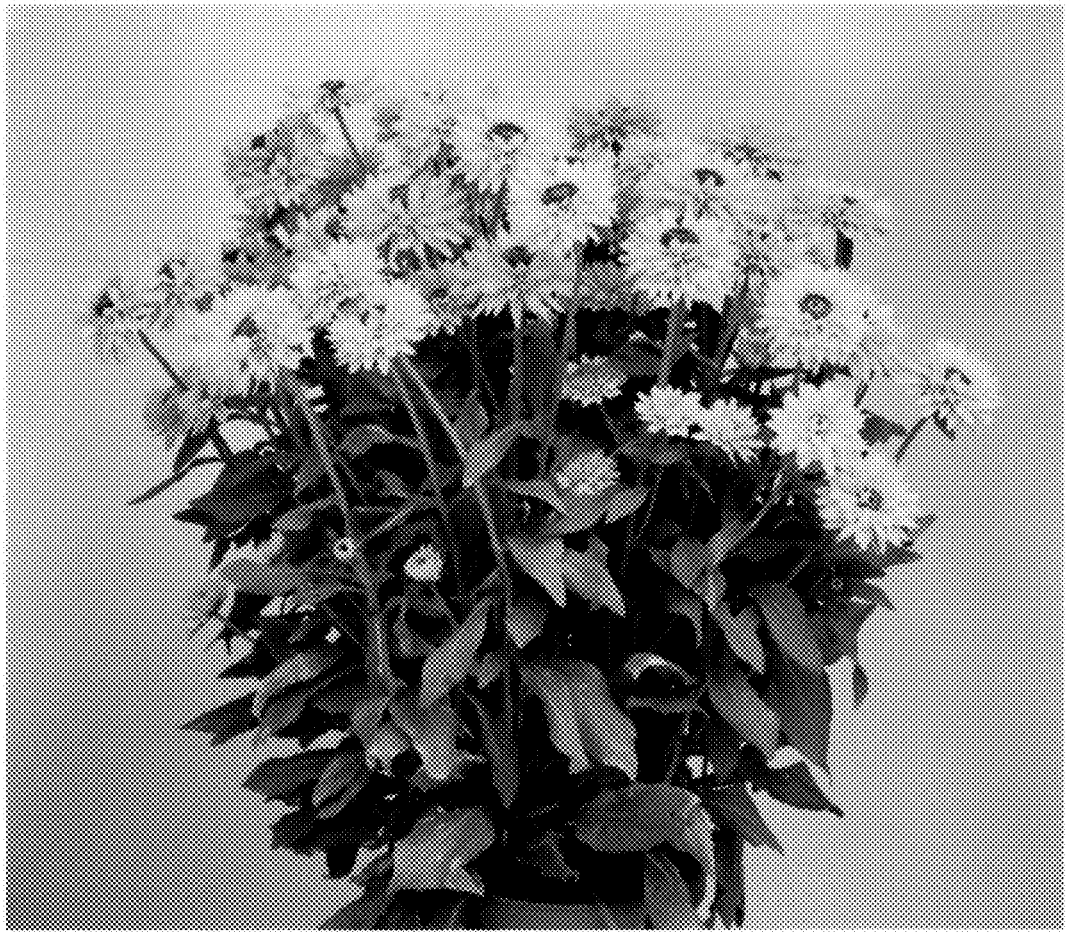
Figure 2:
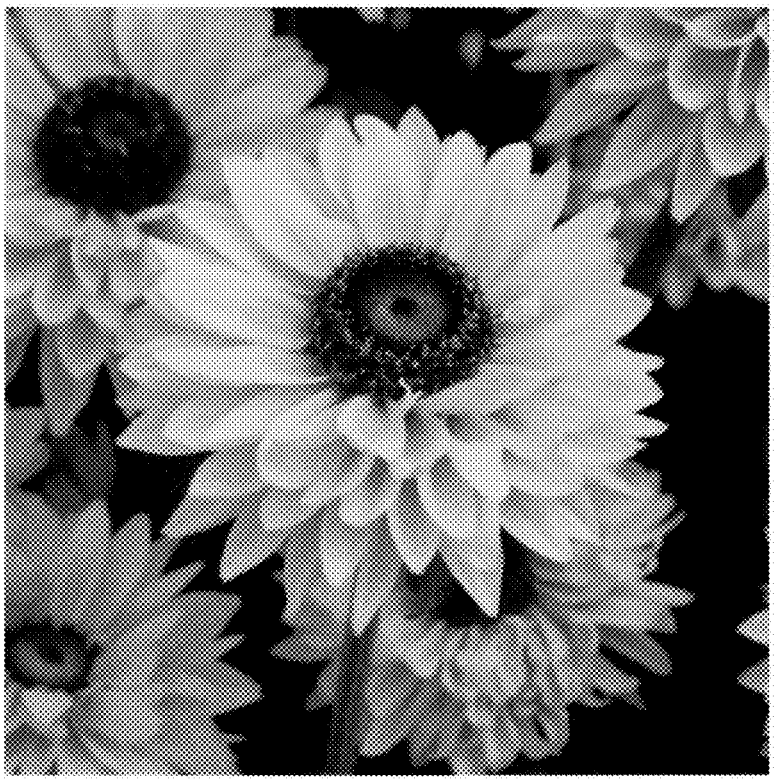

The photograph in FIG. 2 provides a close-up view of an inflorescence of 'RUDBBCH767'.

Figure 3:
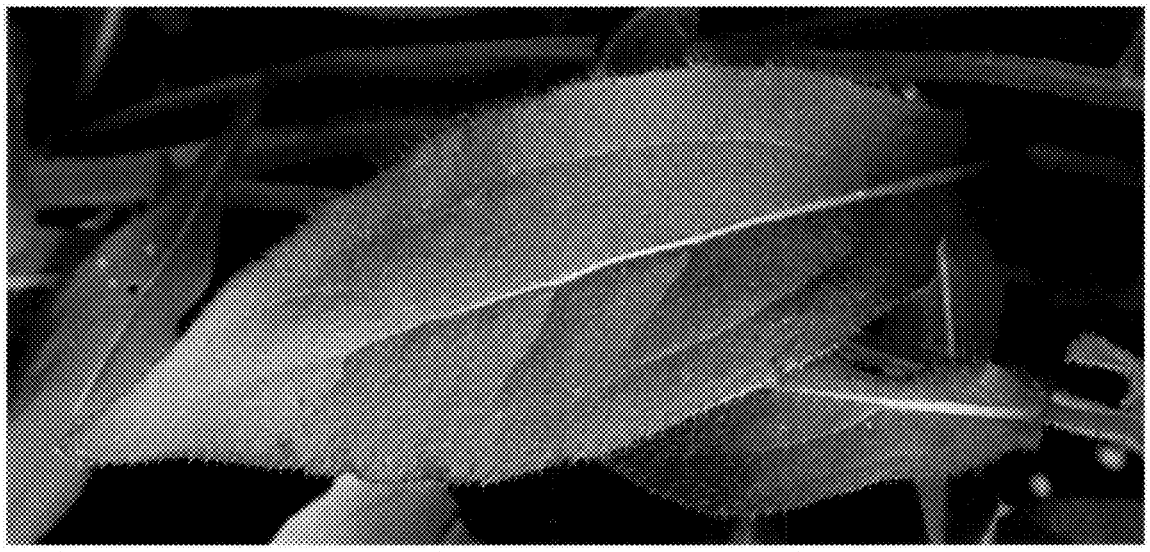

The photograph in FIG. 3 provides a close-up view of a leaf of 'RUDBBCH767'.

The colors in the photographs are as close as possible with the photographic and printing technology utilized and the color values cited in the detailed botanical description accurately describe the colors of the new *Rudbeckia*.

BOTANICAL DESCRIPTION OF THE PLANT

The following is a detailed description of 3-month-old plants of 'RUDBBCH767' as grown outdoors in 23-cm containers in Zuidwolde, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England (2019 reprint), except where general color terms of ordinary dictionary significance are used.

General description:

*Blooming period*.—June to July in The Netherlands.

*Plant type*.—Perennial.

*Plant habit*.—Upright, compact.

*Plant shape*.—Broadly obovate.

*Height and spread*.—Average of 54.4 cm in height from soil level to top of foliar plane and 66.8 cm in height from soil level to top of floral plane, 68.5 cm in diameter as a 3-month-old plant grown in a container.

*Hardiness*.—At least in U.S.D.A. Zones 4 to 10.

*Diseases and pests*.—No susceptibility or resistance to diseases or pests has been observed.

*Root description*.—Fine and fibrous.

*Propagation*.—Tissue culture.

*Root development*.—An average of 2 weeks for root initiation with a young rooted plant produced in an average of 4 weeks.

*Growth rate and vigor*.—Vigorous.

Stem description:

*Shape*.—Very slightly ridged, 5-sided.

*Stem color*.—Young stems; 144B, mature stems; 143A, slightly darker at ridges 144A and 144B.

*Stem size*.—An average of 7 mm in diameter and an average of 26.6 cm in length.

*Stem surface*.—Moderately glossy and densely covered with strigose hairs; an average of 2 mm in length and NN155D in color.

*Stem number*.—Average of 14 main stems, 4 lateral branches per main stem.

*Internode length*.—An average of 4.6 cm in length.

*Stem aspect*.—Main stems; average of 15° to vertical, lateral branches; average of 25° to main stems.

*Branching*.—Freely branching from base with lateral stems.

Foliage description:

*Leaf shape*.—Obovate to narrow obovate.

*Leaf division*.—Simple.

*Leaf base*.—Long cuneate.

*Leaf apex*.—Acute.

*Leaf venation*.—Pinnate, color upper surface 147C, color lower surface 146A.

*Leaf margins*.—Coarsely shallowly crenate-serrate, slightly undulate.

*Leaf attachment*.—Petiolate.

*Leaf arrangement*.—Alternate.

*Leaf size*.—Average of 16.2 cm in length and 5 cm in width.

*Leaf color*.—Young upper surface; 143B, young lower surface; 143C, mature upper surface; 137B, mature lower surface; 147B.

*Leaf surface*.—Upper surface very slightly glossy, lower surface slightly glossy, both surfaces rough to the touch, densely pubescent with short strigose hairs; an average of 1.5 mm in length and N155A in color.

*Petioles*.—Average of 1.4 mm in length, flattened, average diameter at widest point 9 mm and at narrowest point 4 mm, upper and lower surface color; 144A, both surfaces slightly glossy and densely covered with strigose hairs; an average of 1.5 mm in length and 156D in color.

Flower description:

*Type*.—Terminal capitulum, consisting of ray florets and disc florets.

*Capitulum number*.—2 per stem, up to 112 per plant.

*Lastingness of inflorescence*.—Average of 2 weeks, persistent.

*Capitulum size*.—Matures to about 1 cm in height and 9 mm in diameter, disc size is an average of 2.6 cm in diameter.

*Fragrance*.—None.

*Involucral bracts (phyllaries)*.—Cuneate base, bluntly acute apex, narrow oblong in shape, entire margins, average of 30 arranged in 2 rows, rotate, slightly curved downward in an angle of −10°, 2 cm in length and 4.5 mm in width, color; upper surface when fully open 137B, lower surface when fully open 143A, upper surface is matte, lower surface is slightly glossy, all surfaces including margins are moderately covered with strigose hairs; an average of 1.5 mm in length and NN155D in color.

*Receptacle*.—Ovate in shape, an average of 1 cm in height, 9 mm in diameter, 157B in color.

*Buds*.—Shape; flattened globular, immature ray florets pointed upward and slightly curled inwards, 2 cm in length, width; excluding involucral bracts 1.7 cm, including involucral bracts 3.8 cm, color on immature ray florets; 151D, color on involucral bracts; upper side of NN137A, lower surface 137B, surfaces are matte and densely covered with strigose hairs; N155A in color, an average of 0.5 mm in length on immature ray florets and 0.15 cm in length on mature florets.

*Peduncle*.—Strong, straight on top of main flowering stem, average of 14.2 cm in length and 6.5 mm in diameter, color; 143A and 144B, surface moderately glossy and densely covered with short strigose hairs; an average of 2 mm in length and 156D in color.

*Ray florets*.—Average of 100, rotate around the disc in 4 rows (whorls), narrow elliptic to narrow elliptic-ovate in shape, average of 4.1 cm in length and 1.4 cm in width, shallow emarginate to emarginate apex, cuneate base, entire margins, both surfaces are glabrous and velvety, densely covered with very short hairs, 0.5 mm in length and 4D in color, held in varying angles between 30° and −30°, color; when opening upper surface 9A, lower $2/5^{th}$ 17A, when opening lower surface 3A, lower $2/5^{th}$ 15B, when fully open upper surface 12A, lower $2/5^{th}$ 21A, veins 144C, when opening lower surface 13A, lower $2/5^{th}$ 15A, veins 144C.

*Disc florets*.—Average of 800, 20 whorls arranged spirally on a conical receptacle, lower 85% fused into tube, tubular, upright, 9 mm in length and 3 mm in width, tubular, upper 15% free, free lobes have entire margins, apices of free lobes acute and curled backwards, both surfaces glabrous and slightly glossy, color; when opening and fully open upper and lower surface 200A, lower half 155C, no spines, but a single bract is placed beside each disc floret; 1 per disc floret, flattened, an average of 7 mm in length and 1.5 mm in diameter, oblanceolate in shape, acute apex, narrowly cuneate base, color; apex N186C, mid-section 145D, narrowly margined N186C, base 157D, matte surface and moderately pubescent with hairs; an average of 0.2 mm in length, N186C in color.

Reproductive organs (present on disc florets only):

*Gynoecium*.—Pistil; 1, 6 mm in length, style; 5 mm in length, 157D in color, stigma; cleft, decurrent, 3 mm in diameter, 200A in color, ovary; 197C in color.

*Androecium*.—Stamens; 5, filaments; 2 mm in length, 155A in color, anther; narrow oblong in shape, 2.5 mm in length, 0.5 mm in width, 200A in color, pollen; moderate in quantity and 15A in color.

*Fruit/seed*.—None observed to date.

It is claimed:

1. A new and distinct cultivar of *Rudbeckia* plant named 'RUDBBCH767' substantially as herein illustrated and described.

* * * * *